United States Patent

Hawkes et al.

[11] 4,233,155
[45] Nov. 11, 1980

[54] APPARATUSES FOR THE ANAEROBIC DIGESTION OF NATURAL ORGANIC WASTE

[75] Inventors: Dennis L. Hawkes; Rex Horton, both of Mid-Glamorgan; David A. Stafford, Cardiff, all of Wales

[73] Assignee: Hamworthy Engineering Limited, Fleets Corner, England

[21] Appl. No.: 963,095

[22] Filed: Nov. 22, 1978

[51] Int. Cl.³ .............................................. B01D 55/14
[52] U.S. Cl. ..................................... 210/92; 210/198; 210/218; 210/258; 210/532 S
[58] Field of Search ............... 210/198, 205, 209, 218, 210/416, 260, 297, 274, 92, 523, 526, 536; 435/284, 290, 313, 292, 813, 801, 302, 287, 309, 310

[56] References Cited

U.S. PATENT DOCUMENTS

| 24,219 | 9/1856 | Pirnie | 210/205 |
|---|---|---|---|
| 585,121 | 6/1897 | Righter | 210/297 |
| 1,416,899 | 5/1922 | Sirch | 210/536 |
| 2,057,567 | 10/1936 | Fries | 210/536 |
| 2,220,574 | 11/1940 | Little et al. | 210/526 |
| 2,382,080 | 8/1945 | Lowry | 210/416 R |
| 2,394,076 | 2/1946 | Kisch | 210/416 R |
| 3,211,535 | 10/1965 | Hirahara | 210/205 X |
| 3,341,115 | 9/1967 | Beck et al. | 210/416 R |
| 3,576,251 | 4/1971 | Clyne | 210/526 |
| 3,765,535 | 10/1973 | Anderson et al. | 210/274 |
| 4,100,023 | 7/1978 | McDonald | 435/813 |
| 4,100,070 | 7/1978 | White et al. | 210/274 |

Primary Examiner—Theodore A. Granger
Attorney, Agent, or Firm—Parmelee, Miller, Welsh & Kratz

[57] ABSTRACT

An apparatus for the anaerobic digestion of natural organic waste comprises a feed tank, a digester and an outlet tank. There is further provided feed means which feeds waste to be digested from the feed tank to the digester at an adjustable continuous rate. A gas pump may be used to recirculate from the top of the digester through a diffuser to the bottom of the digester. A suitable gas pump comprises a container partially filled with liquid so as to provide a space above the liquid surface and within the container sealed by the liquid from the exterior of the container, pumping means being provided in the said space.

10 Claims, 3 Drawing Figures

APPARATUSES FOR THE ANAEROBIC DIGESTION OF NATURAL ORGANIC WASTE

BACKGROUND OF THE INVENTION

1. Field of the Invention

The present invention relates to apparatuses for the anaerobic digestion of natural organic waste.

2. Description of the Prior Art

In a known sewage treatment apparatus, sewage for treatment is loaded into a digester in batches at intervals so as to give a hydraulic retention time of from 20 to 40 days. This type of loading can produce a shock load on the microbial population by causing an accumulation of volatile fatty acid which can be toxic to the methane-producing bacteria. It is thought that these long retention times of 20 to 40 days are thus necessary for the bacterial population to acclimatise to the changing environment imposed upon them by this type of feeding mechanism.

SUMMARY OF THE INVENTION

According to one aspect of the present invention, there is provided an apparatus for the anaerobic digestion of natural organic waste, comprising a feed tank, a digester, and an outlet tank, there being provided feed means arranged to feed waste to be digested from the feed tank to the digester at an adjustable continuous rate.

The feed means may comprise a bucket elevator, arranged to remove waste from the feed tank, and a loading tube, arranged to receive waste from the bucket elevator and to direct it under gravity into the digester.

According to another aspect of the present invention, there is provided a gas pump comprising a container partially filled with liquid so as to provide a space above the liquid surface sealed by the liquid from the exterior of the container, pumping means being provided in the said space.

The pumping means may comprise a piston and cylinder, which may be double acting.

Figure 1:
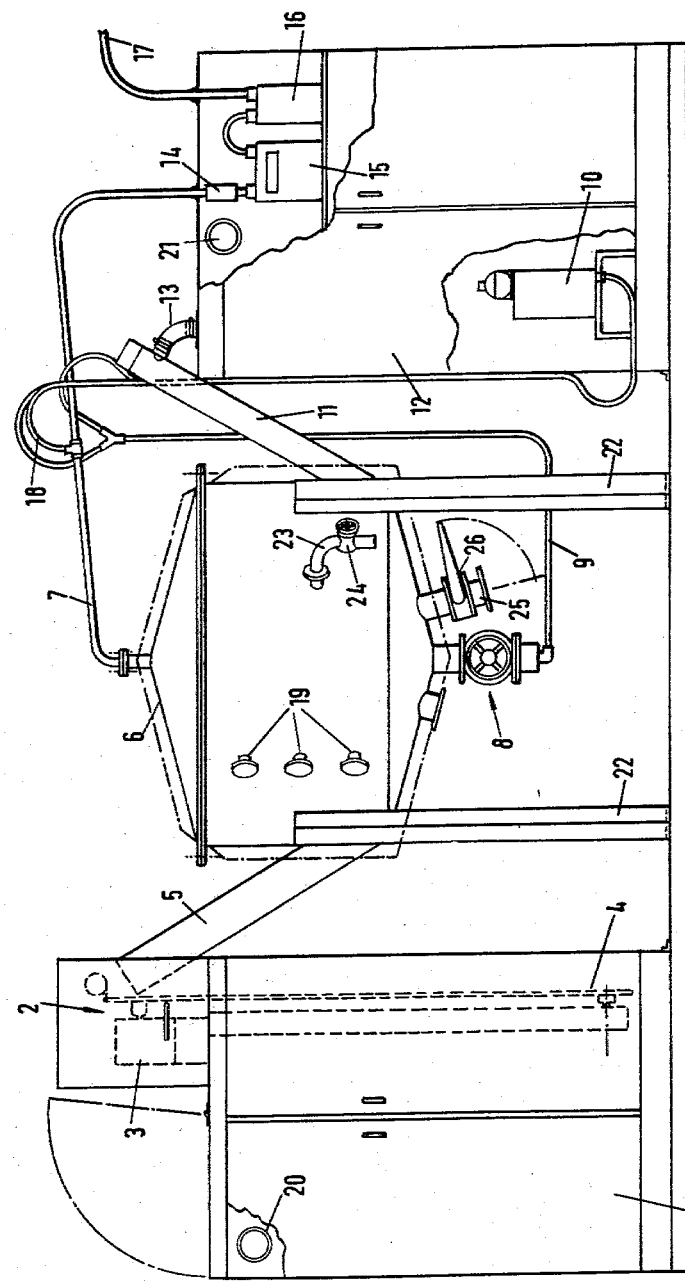
FIG. 1 is a side elevation of a preferred apparatus for the anaerobic digestion of natural organic waste.
Figure 2:
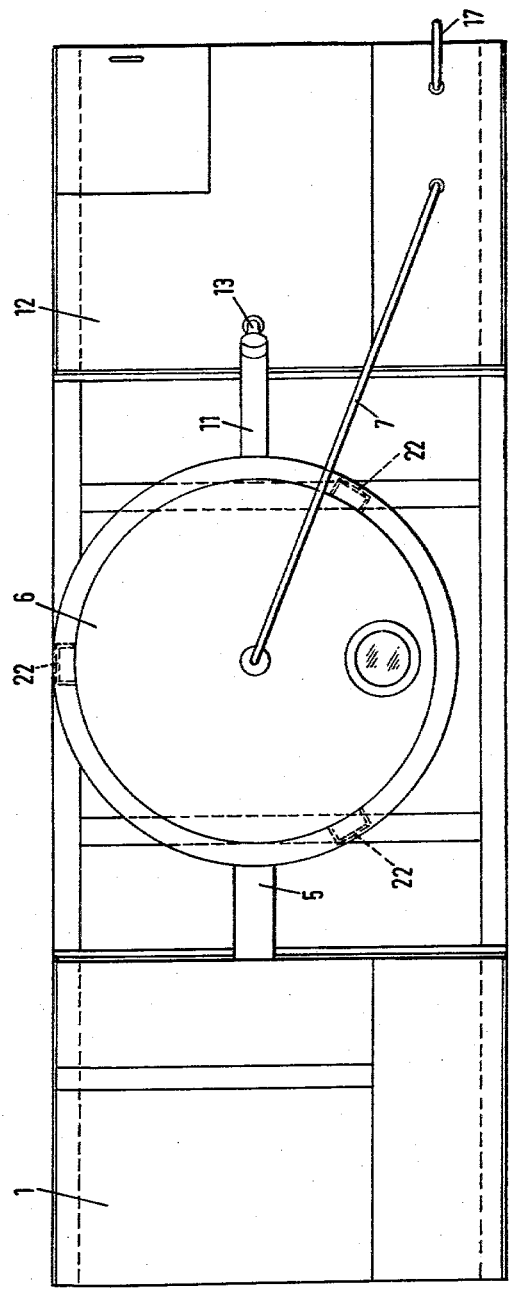
FIG. 2 is a plan view of the apparatus of FIG. 1.

The preferred apparatus comprises a feed tank 1 into which waste for treatment can be loaded including a bucket elevator 2. The bucket elevator 2 comprises an electric motor 3 arranged to drive an endless belt 4 on which are provided a plurality of buckets. The buckets are arranged to scoop waste from within the feed tank 1 and to empty the waste into a loading tube 5.

The loading tube 5 extends downwardly from the bucket elevator 2 into a digester 6 which is mounted on three pillars 22. The digester 6 has a gas outlet pipe 7 for removal of gases such as methane which collect over the fluid in the digester as a result of bacterial activity therein. A diffuser 8 is provided at the bottom of the digester 6 and is connected via a pipe 9 to a gas pump 10. The diffuser 8 end incorporates a flexible membrane perforated with fine holes. These holes are such that they only open when pressurized by gas recirculated from the gas pump 10 so that they do not become clogged. Alternatively, the diffuser 8 may consist of a solid diffuser.

An outlet tube 11 extends upwardly from the digester 6 and is open to the atmosphere at its upper end. Adjacent its upper end, the outlet tube 11 is connected to an outlet tank 12 via a flexible hose 13.

The gas outlet pipe 7 is connected via a flame arrester 14 to a digital gas meter 15, whose outlet is connected to a digester pressure regulator 16. Gas from the pressure regulator 16 is then connected via a pipe 17, for instance, to a gas stack or gasometer. The outlet pipe 7 is also connected via a pipe 18 to an inlet of the gas pump 10.

Thermocouples and/or thermistors 19 are provided in the digester 6 for monitoring the temperature of the fluid therein. Gas alarms 20 and 21 are provided on the feed tank and the outlet tank, respectively. A discharge pipe 23 and valve 24 are provided on the side of the digester 6 for sampling and a discharge tube 25 and valve 26 are provided on the bottom of the digester for removal of digested sludge.

Figure 3:
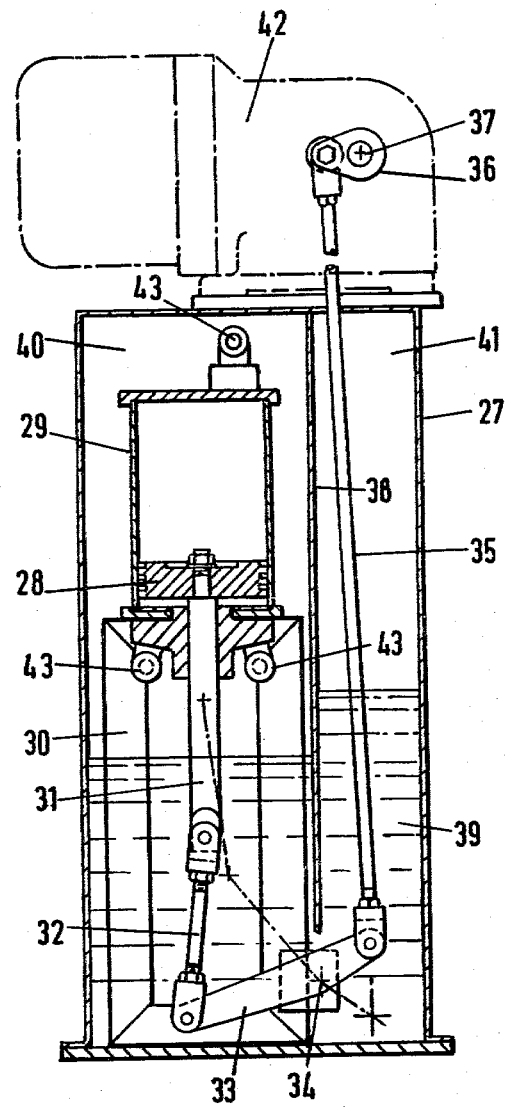
FIG. 3 is a cross-sectioned side view of a gas pump of the apparatus of FIG. 1.

The gas pump 10 is shown to a larger scale in cross-section in FIG. 3 and comprises a vessel 27 containing a double acting piston 28 and cylinder 29 mounted on a frame 30. The piston 28 is connected via a piston rod 31 and a coupling rod 32 to a first end of a rocking lever 33 which is pivotable about an axis 34. The other end of the rocking lever 33 is pivotably connected to one end of a driving link 35 whose other end is connected to a crank 36 (shown rotationally out of position for the sake of clarity). The crank 36 is mounted on a shaft 37 of a prime mover, such as an electric motor with a reduction drive 42.

The prime mover is separated from the piston 28 and cylinder 29 by a dividing wall 38 and liquid 39. The level of the liquid 39 on either side of the dividing wall 38 is such that the bottom of the dividing wall is below the liquid surface, so that the space 40 above the liquid and containing the cylinder 29 is air-tightly sealed from the space 41, which communicates with the atmosphere via a duct in the vessel 27.

The cylinder 29 is connected via valves (not shown) and pipes 43 to the pipes 9 and 18 so as to draw gas from the pipe 18 into the cylinder 29 on alternate sides of the piston 28 during consecutive strokes thereof and to force gas into the pipe 9 with alternate strokes of the double acting piston.

In use, waste is fed into the feed tank 1, from which it is continuously loaded into the digester 6 at a suitable predetermined rate by means of the bucket elevator 2 and the loading tube 5.

The temperature of the contents of the digester is substantially maintained at a predetermined value, usually between 20° and 60° C., depending on the type of waste to be treated. This can be achieved automatically by providing a control system arranged to control heating means provided in the digester according to the outputs from the thermo-couples and/or thermistors 19.

Gases such as methane and carbon dioxide are given off during the digestion of waste by the bacteria and are fed via the gas outlet pipe 7 to the gas pump 10 and to the gas stack or gasometer. The gas which is fed to the gas pump 10 is returned under pressure to the digester 6 via the pipe 9 and the diffuser 8. The inflow of gas via the diffuser produces efficient mixing of the contents of the digester and allows intimate contact between the gas and the bacteria, thus improving the efficiency of the digester.

The arrangement of the outlet tube 11, which acts as a settling vessel, encourages the maintaining of a suitable bacterial population in the digester, solid particles therein settling back into the digester under gravity. This permits a shorter hydraulic retention time for the liquids to be used, thus allowing a digester of smaller volume to be used. The solids are held in the digester for a relatively longer period allowing for more complete digestion and increasing the bacterial population.

Treated waste is fed from the digester 6 via the outlet tube 11 to the outlet tank 12, from which it may be discharged in any required way. Accumulated sludge can be removed from the bottom of the digester via the discharge tube 25 and the valve 26 and can be run off via the discharge pipe 23 and the valve 24.

The bucket elevator 2 allows water comprising organic material of almost any moisture content to be treated. The feeding rate is variable so as to cater for different types of waste and for the required retention time. Gravity feed of the digester 6 via the loading tube 5 has the advantage that no seals or valves are required and is thus relatively simple and reliable and makes any malfunction visibly obvious.

Excessive pressure build up within the digester 7 is prevented because the loading tube 5 and the outlet tube 11 are open to the atmosphere. A workable pressure can be maintained in the apparatus by means of a predetermined head of water in a digester pressure regulator (not shown).

The gas pump 10 is relatively simple and easy to maintain. The use of the liquid 39 acting as a hydraulic seal to prevent escape to the atmosphere of gas leaking through piston seals provided between the piston 28 or the piston rod 31 and the cylinder 29 makes the gas pump intrinsically safe.

The present apparatus can be of modular construction and can be made in batch production quantities to cater for a range of required sizes. However, various mechanisms, such as those for loading, mixing or temperature control, can be standard items.

Various modifications may be made within the scope of the invention. For instance, the digester 6 may be provided with a floating top, instead of a fixed top as shown, to provide a substantially constant gas pressure therein. Also, the bucket elevator 2 may be replaced by a pump to feed organic waste material into the digester 6.

We claim:

1. Apparatus for the anaerobic digestion of natural organic waste comprising a closed container in which the organic waste can be retained while the anaerobic microrganism present in the waste digests the same, a feed tube which extends downward into said container on one side thereof and through which said natural organic waste is introduced into said container, an inclined outlet tube which extends upward from the container on the opposit side thereof to a point higher than the lower end of said inlet tube such that the liquid level in the container remains above the ends of the inlet and outlet tubes which communicate with the container and hence the space in the container above the liquid level is sealed from the atmosphere by said liquid, the inclination of said outlet tube being such that as waste is introduced into the container through the feed tube and the liquid overflows through the outlet tube, solids which have not settled to the bottom of the container settle onto the inclined wall of the outlet tube and remain in the container, a gas outlet in the top of the closed container through which the gases produced by digestion of the organic waste are collected; a diffuser located in the bottom of said container, a gas pump for pumping the collected gases through said diffuser, means establishing communication between said gas outlet and sid gas pump, and means establishing communication between said gas pump and diffuser beneath the container, said diffuser comprising a flexible membrane perforated with holes which are sufficiently fine to open only when pressurized by gas from said gas pump, whereby efficient mixing of the contents and intimate contact between gas and bacteria therein is effected, improving the efficiency of anaerobic digestion of waste in the container.

2. An apparatus as set forth in claim 1, wherein there is provided a feed tank and feed means for feeding waste to be digested from said feed tank to said feed tube and into said container at an adjustable continuous rate, said feed means comprising a bucket elevator.

3. An apparatus as set forth in claim 2, wherein said bucket elevator comprises an electric motor driving an endless belt on which are provided a plurality of buckets.

4. An apparatus as set forth in claim 1, wherein said outlet tube has an open upper end and communicates adjacent said upper end with an outlet tank.

5. An apparatus as set forth in claim 1, wherein said container has a side provided with a discharge pipe including a valve for allowing a sample of the contents of said container to be removed.

6. An apparatus as set forth in claim 1, wherein said container has a bottom provided with a discharge tube including a valve for permitting removal of sludge from said container.

7. An apparatus as set forth in claim 1, wherein said container includes a movable upper part free to move under the influence of gas generated in said container.

8. An apparatus as set forth in claim 1, wherein said container has upper and lower convex conical portions joined together by a cylindrical portion.

9. An apparatus as set forth in claim 1, wherein said gas pump comprises a further container partially filled with liquid so as to define a space above the liquid surface sealed by the liquid from the exterior of the further container, pumping means being provided in said space.

10. An apparatus as set forth in claim 1, wherein said pumping means comprises a double acting piston and cylinder connected via valves to said gas outlet and said diffuser, and wherein said further container includes a first portion which has an open top and which is divided from a second portion containing said pumping means by a wall which extends below the normal liquid working level in said further container.

* * * * *